Figure 1:
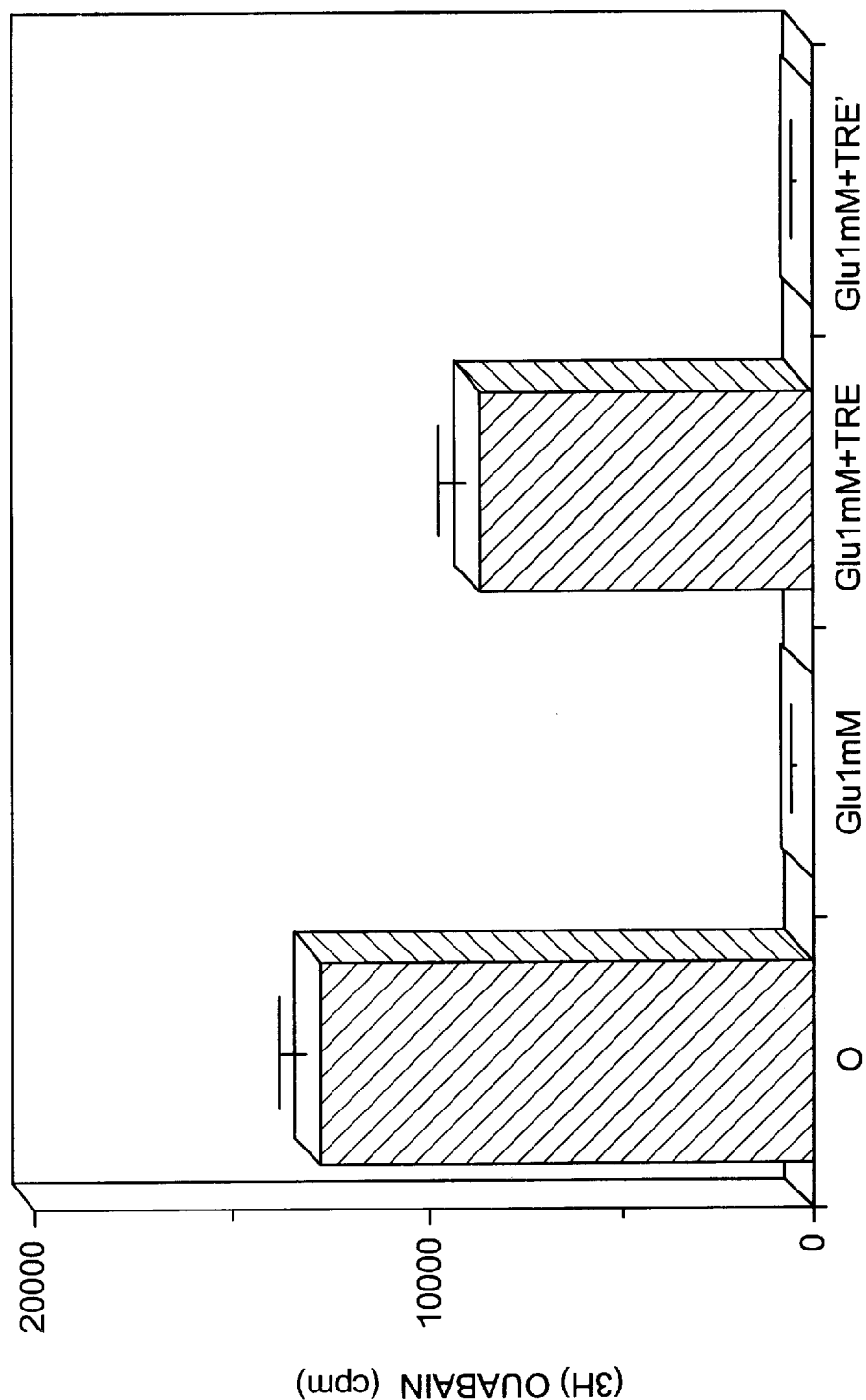

United States Patent [19]
Mallet et al.

[11] Patent Number: 6,140,112
[45] Date of Patent: Oct. 31, 2000

[54] PHARMACEUTICAL COMPOSITIONS AND THEIR USE, NAMELY FOR THE TREATMENT OF NEURODEGENERATIVE DISEASES

[75] Inventors: Jacques Mallet, Paris; Frédéric Revah, Antony; Jean-Jacques Robert, Sceaux, all of France

[73] Assignee: Rhone-Poulenc Rorer S.A., Antony, France

[21] Appl. No.: 08/569,149

[22] PCT Filed: Jun. 27, 1994

[86] PCT No.: PCT/FR94/00771

§ 371 Date: Apr. 25, 1996

§ 102(e) Date: Apr. 25, 1996

[87] PCT Pub. No.: WO95/01429

PCT Pub. Date: Jan. 12, 1995

[30] Foreign Application Priority Data

Jun. 30, 1993 [FR] France .................................. 93 07962

[51] Int. Cl.⁷ ............................. C07H 21/04; C12N 15/63
[52] U.S. Cl. ........................... 435/320.1; 435/6; 435/91.3; 435/91.31; 536/23.1; 536/24.1; 536/24.5
[58] Field of Search ............................ 435/6, 91.3, 91.31, 435/172.3, 320.1; 514/44; 536/233.1, 24.1, 24.5

[56] References Cited

FOREIGN PATENT DOCUMENTS

WO 92/19732  4/1991  WIPO .

OTHER PUBLICATIONS

Angel et al. "Phorbol Ester–Inducible Genes Contain a Common Cis Element Recognized by a TPA–Modulated Trans–Acting Factor" Cell, vol. 49: 729–739, Jun. 19, 1987.

Karin et al. "Metal–Responsive Elements Act as Positive Modulators of Human Metallothionine–IIA Enhancer Activity" Molecular and Cellular Biology vol. 7(2): 606–613, Feb. 1987.

Byrnes, A.P. et al "Adenovirus Gene Transfer Causes Inflamation in the Brain" Neuroscience, vol. 66, No. 4 pp. 1015–1024 1995.

Benson et al "General Selection for Specific DNA–Binding Activities". Genetics. vol. 114, No. 1 pp. 1–14 1986.

Stull et al "Antigene, Ribozyme and Aptamer Nucleic Acid Drugs: Progress & Prospects". Pharmaceutical Research vol. 12, No. 4 pp. 465–483 1995.

Lasil, D. "Liposomes within Liposomes", Nature vol. 387: 26–27, May 1, 1997.

Orkin et al "Report and Recomendations of the Pane to Assess the NiH Invesment in Research on Gene Therapy", Dec. 7, 1995.

*Primary Examiner*—David Guzo
*Assistant Examiner*—Sean McGarry
*Attorney, Agent, or Firm*—Finnegan, Henderson, Farabow, Garrett & Dunner, L.L.P.

[57] ABSTRACT

The present invention pertains to the use of compounds affecting the activity of transcription factors for the preparation of a pharmaceutical composition for the treatment of neurodegenerative diseases.

4 Claims, 3 Drawing Sheets

SEQUENCE LISTING

```
(1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

AGCCGCAAGT GACTCAGCGC GGGGC                                              25
```

PHARMACEUTICAL COMPOSITIONS AND THEIR USE, NAMELY FOR THE TREATMENT OF NEURODEGENERATIVE DISEASES

The present invention relates to pharmaceutical compositions and to their use, in particular for the treatment of neurodegenerative diseases. It relates more especially to the use of compounds which act on the interaction between the sequence SEQ ID No. 1 and transcription factors for the preparation of a pharmaceutical composition intended for the treatment of neurodegenerative diseases.

The present invention is partly the outcome of the demonstration that the factor AP1 constitutes a mediator of neuronal degeneration, and that the use of compounds capable of inhibiting the activity of this complex can enable the process of neuronal death to be blocked. It is also the outcome of the demonstration that nucleic acids corresponding to the site of interaction of a transcription factor with DNA are capable of at least partially inhibiting the activity of this transcription factor.

To study the molecular mechanisms of neuronal degeneration, the Applicant used glutamate-induced toxicity as a model. Glutamate is the main excitatory neurotransmitter of the central nervous system. However, exposure to glutamate for abnormally long periods, or at concentrations higher than the physiological concentrations, may cause a neuronal toxicity designated by the term excitotoxicity (Olney Adv. Exp. Med. Biol. 203 (1986) 631). Many experimentally based lines of reasoning suggest that this type of toxicity contributes to the neuronal degeneration associated with ischaemia, hypoxia, hypoglycaemia and epileptic fits, or alternatively with cerebral trauma (Choi, J. Neurobiol. 23 (1992) 1261). Excitotoxicity is also considered to be involved in the pathogenesis of diseases such as Huntington's chorea (Young et al., Science 241 (1988) 981) and Alzheimer's disease (Koh et al., Brain Res. 533 (1990) 315; Mattson et al.; J. Neurosci. 12 (1992) 376).

More specifically, the Applicant studied the death induced by glutamate on embryonic rat cortical neurons in primary culture. Previous work had enabled it to be shown that the binding of glutamate to its membrane receptors caused depolarization of the cell membrane and an increase in intracellular calcium, which leads to the activation of a cascade of second messengers involving several families of enzymes. The Applicant studied at genetic level the modulation of the early response genes coding for transcription factors which, interacting in their turn with regulatory sequences of certain genes, will activate or repress their expression. More especially, the Applicant was able to show, surprisingly, that exposure of cortical cells to glutamate or to other excitotoxins such as NMDA causes an increase in the number of protein complexes capable of binding to the genomic sequence designated "12-O-tetradecanoylphorbol 13-acetate-responsive element", abbreviated to TRE [Schöntal et al., Cell 54 (1988) 325; Lucibello et al., Oncogene 3 (1988) 43; Angel et al., Cell 49 (1987) 729; Bohman et al., Science 238 (1988) 1386]. This sequence of the TRE region is shown in SEQ ID No. 1. Furthermore, the Applicant also showed that, by sequestering the factors capable of binding to the sequence SEQ ID No. 1, cortical cells are saved from death induced by certain ranges of glutamate concentrations. This demonstrates that the sequence SEQ ID No. 1 plays the part of a mediator of neuronal degeneration, an observation which has never been reported in the prior art. The sequence SEQ ID No. 1 and the set of transcription factors capable of interacting with it hence constitutes a new pharmacological target in the treatment of neurodegenerative processes. Hence the invention lies in part in the use of compounds capable of blocking the activity of the sequence SEQ ID No. 1 for the treatment of neurodegenerative diseases.

Hence a first subject of the present invention lies in the use of a compound which at least partially inhibits the interaction between the sequence SEQ ID No. 1 and the transcription factors which interact with it, for the preparation of a pharmaceutical composition intended for the treatment and/or prevention of neurodegenerative diseases.

The compounds which at least partially inhibit the interaction between the sequence SEQ ID No. 1 and the transcription factors, for the purposes of the present invention, may be compounds which act, for example, (i) on the synthesis of these factors or of their components, at transcriptional, translational or post-translational levels, (ii) on the molecular mechanisms of modulation of the activity of these factors (multimerization, phosphorylation-dephosphorylation, and the like), or alternatively, (iii) on the binding of these factors to the sequence SEQ ID No. 1.

The transcription factors which interact with the sequence SEQ ID No. 1 have been grouped together under the generic term AP1 (Landschultz et al., Science 240 (1988) 1759). The molecules in question are dimers whose unit components are linked to one another through a "leucine zipper" structural motif. Typically, one of the components belongs to the family of Fos proto-oncogenes (family comprising, in particular, the proteins Fos, Fra1, Fra2 and FosB) and the other to the Jun family (family comprising, in particular, the proteins Jun, JunB and JunD). As an example, the Fos protein is composed of 380 amino acids, Jun of 354 (review in Mc Mahon and Monroe, FASEB J. 6 (1992) 2707).

Among the compounds which act on the synthesis of factors binding to the sequence SEQ ID No. 1, the antisense nucleotide sequences directed against these factors or their components, which inhibit the translation of the corresponding genes, may be mentioned. Thus, in the case of Fos and Jun, it is possible to use the antisense sequences described by Holt et al. (PNAS 83 (1986) 4794) or by Kovary and Bravo (Mol. Cell. Biol. 11 (1991) 4466). Other compounds which act on the regulation of the expression of the genes for these factors may also be mentioned in the context of the invention, such as, in particular, curcumin (Huang et al., PNAS 88 (1991) 5292), 2-aminopurine (Zinn et al., Science 240 (1988) 210) or alternatively heparin (Wright et al., PNAS 86 (1989) 3199), which compounds are capable of acting on the synthesis of Fos and of Jun.

Another class of compounds which can be used in the context of the present invention groups together the compounds which act on the molecular mechanisms of modulation of the activity of the transcription factors which interact with the sequence SEQ ID No. 1. These mechanisms involve, in particular, steps of multimerization, phosphorylation-dephosphorylation, and the like. As regards the factor AP1, the latter, in order to be active, has to be phosphorylated, the phosphorylation being catalyzed by protein kinase C or protein kinase A (review in Mc Mahon and Monroe cited above), as well as by a DNA-dependent protein kinase (Bannister et al., Nucleic Acids Res. 21 (1993) 1289). Among the compounds which act on the phosphorylation of AP1 for the purposes of the invention, compounds capable of at least partially inhibiting the activity of these protein kinases may hence be mentioned.

Finally, as stated above, other compounds, for the purposes of the present invention, are those capable of at least partially inhibiting the interaction between the transcription factors and the sequence SEQ ID No. 1. Such compounds can be, in particular, transcription factor antagonists, or proteins capable of interacting with the transcription factors or their components or the sequence ID No. 1 and of thus modulating the activity of binding between these factors and the sequence SEQ ID No. 1. In this connection, the proteins of the family CREB (Hai and Curran, PNAS 88 (1991) 3720), LRF-1 (Hsu et al., PNAS 88 (1991) 3511), and IP-1 (Auwerx and Sassone-Corsi, Cell 64 (1991) 983), or steroid receptors (review in Miner and Yamamoto, Trends in Biochem. Sci. 16 (1991) 423), may be mentioned. The members of the CREB family interact with the monomers of the Fos or Jun family. The different heterodimers have different binding specificity. Thus, the Fos-CREB or Jun-CREB cross-dimers may bind to the TRE site, but also to the CRE site (site of binding of the CREB proteins to DNA), depending on the composition of the dimer. More specifically, they generally display a preferential binding to the CRE site (Hai and Curran, cited above). The dimerization of a member of the CREB family with a member of the Fos or Jun family hence induces a modulation of the number of factors bound to the sequence SEQ ID No. 1. The LRF-1 protein forms dimers with c-Jun and Jun-B. These dimers are capable of binding in vitro to the CRE site and, as a result, of interfering with the number of factors bound to the sequence SEQ ID No. 1 (Hsu et al., cited above). IP-1 is an endogenous factor appearing in the nucleus and the cytoplasm of several cell types. IP-1 specifically blocks the binding of AP1 factors to DNA. It is a protein of 30 to 40 kDa which exerts its activity when in phosphorylated form (Auwerx and Sassone-Corsi, cited above). As regards receptors for steroids (glucocorticoids, mineralocorticoids, progesterone, androgens, and the like), these are nuclear receptors which belong to the family of zinc finger transcription factors. They possess sites of interaction with DNA which are different from SEQ ID No. 1. However, there are composite response elements in the regulatory regions of the genes, with which elements the members of the steroid receptor family and members of the leucine zipper transcription factor family (AP1, CREB, LRF-1, and the like) can interact (via protein-protein or protein-DNA interactions) to produce regulatory effects which do not exist in the presence of only one of these factors. For these reasons, since this set of proteins is capable of interacting directly or indirectly with the AP1 factors and/or the sequence SEQ ID No. 1, these proteins may be used in the context of the present invention to inhibit the process of neuronal degeneration. These proteins may be used as they are or in the form of genetic constructions capable of expressing these proteins in vivo. Other compounds capable of at least partially inhibiting the interaction between the transcription factors and the sequence SEQ ID No. 1 consist of double-stranded nucleic acids reproducing the site of binding of the transcription factors to DNA, that is to say the sequence SEQ ID No. 1, or any active variant of the latter. The Applicant showed, in effect, that such nucleic acids were capable of complexing the transcription factors (and especially the factor AP1) present in cells, of preventing them from binding to their endogenous sites, and thus of blocking their transcriptional activity.

In a preferred embodiment, the compound used in the context of the present invention is a double-stranded nucleic acid comprising all or part of the sequence SEQ ID No. 1 or of an active variant of the latter.

The term active variant denotes, for the purposes of the invention, any variant of the sequence SEQ ID No. 1 which has retained the properties of binding to the factor AP1. Such variants may be obtained by mutation, deletion, substitution and/or addition of bases on the sequence SEQ ID No. 1, followed by in vitro verification of the binding activity, as described in Examples 1 and 2.

This double-stranded nucleic acid may be used as it is, for example after injection into humans or animals, to induce a protection or to treat neuronal degeneration. In particular, it may be injected in the form of naked DNA according to the technique described in Application WO 90/11092. It may also be administered in the form of complexes, for example with DEAE-dextran (Pagano et al., J. Virol. 1 (1967) 891), with nuclear proteins (Kaneda et al., Science 243 (1989) 375), with lipids (Felgner et al., PNAS 84 (1987) 7413), in the form of liposomes (Fraley et al., J. Biol. Chem. 255 (1980) 10431), and the like.

Preferably, the double-stranded nucleic acid used in the context of the invention forms part of a vector. The use of such a vector makes it possible, in effect, to improve the administration of the nucleic acid in the cells to be treated, and also to increase its stability in the said cells, thereby enabling a lasting inhibitory effect to be obtained. Furthermore, it is possible to introduce several nucleic acid sequences into the same vector, which also increases the efficacy of the treatment.

The vector used may be of various origins, provided it is capable of transforming animal cells, preferably human nerve cells. In a preferred embodiment of the invention, a viral vector is used, which may be chosen from adenoviruses, retroviruses, adeno-associated viruses (AAV), herpesvirus, and the like.

In this connection, the subject of the present invention is also any recombinant virus comprising, inserted into its genome, a double-stranded nucleic acid corresponding to a site of interaction of a transcription factor with DNA. The present invention demonstrates, in effect, the possibility of treating certain pathologies resulting from the expression of certain genes, not by directly affecting the gene or genes involved, nor their messenger RNAs, nor the product of their translation, but by affecting the activity of the transcription factors responsible for their expression. This approach enables the expression of many genes, such as, for example, that of the gene coding for the different isoforms of the amyloid protein precursor (APP), which is involved in the pathogenesis of Alzheimer's disease, to be controlled. This gene contains, in effect, 2 binding sites for a transcription factor (AP1) less than 400 bp upstream of the transcription startsite (Lee et al., Nature 325 (1987) 368). Similarly, the promoter of the gene for tyrosine hydroxylase, a key enzyme in cathecolamine synthesis, involved in Parkinson's disease, contains a binding site for the factor AP1 (Icard-Liepkans et al., J. Neurosc. Res. 32 (1992) 290). Another example concerns the NGF gene, which also possesses a binding site for a transcription factor (S D'Mello and Heinrich, Mol. Brain Res. 11 (1991) 255).

The recombinant virus according to the invention may be chosen from adenoviruses, retroviruses, adeno-associated viruses, and the like. Preferably, it is a virus capable of infecting nerve cells, such as, in particular, an adenovirus. Vectors derived from adenoviruses, retroviruses, or AAVs incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

In a particular embodiment of the invention, the recombinant viruses such as are defined above comprise a double-stranded nucleic acid corresponding to the site of interaction of the factor AP1 with DNA. Still more preferably, the double-stranded nucleic acid comprises all or part of the sequence SEQ ID No. 1 or of an active variant of the latter.

Advantageously, the recombinant virus according to the invention is a defective virus. The term "defective virus" denotes a virus incapable of replicating in the target cell. Generally, the genome of the defective viruses used in the context of the present invention hence lacks at least the sequences needed for replication of the said virus in the infected cell. These regions may be either removed (wholly or partially), or rendered non-functional, or replaced by other sequences, and in particular by the double-stranded nucleic acid. Preferably, the defective virus nevertheless retains the sequences of its genome which are needed for encapsidation of the viral particles.

It is especially advantageous to use the nucleic acid sequences of the invention in a form in which they are incorporated in a defective recombinant adenovirus.

There exist, in effect, different serotypes of adenovirus, the structure and properties of which vary somewhat, but which are not pathogenic for man, and in particular non-immunosuppressed subjects. Moreover, these viruses do not integrate in the genome of the cells they infect, and can incorporate large fragments of exogenous DNA. Among the different serotypes, it is preferable to use, in the context of the present invention, adenoviruses type 2 or 5 (Ad 2 or Ad 5). In the case of the Ad 5 adenoviruses, the sequences needed for replication are the E1A and E1B regions.

Moreover, the small size of the nucleic acids corresponding to the site of binding to DNA of a transcription factor according to the invention advantageously makes it possible to incorporate simultaneously, in the same vector, several nucleic acids, which may be identical (intended for blocking the same transcription factor) or different (intended for blocking different transcription factors). A particular embodiment of the invention hence consists of a vector, in particular a viral vector, comprising at least two nucleic acids such as are defined above.

The defective recombinant viruses of the invention may be prepared by homologous recombination between a defective virus and a plasmid carrying, inter alia, the nucleic acid sequence such as is defined above (Levrero et al., Gene 101 (1991) 195; Graham, EMBO J. 3(12) (1984) 2917). Homologous recombination takes place after cotransfection of the said virus and said plasmid into a suitable cell line. The cell line used should preferably (i) be transformable by the said elements, and (ii) contain the sequences capable of complementing the portion of the genome of the defective virus, preferably in integrated form in order to avoid risks of recombination. As an example of a line which can be used for the preparation of defective recombinant adenoviruses, the human embryonic kidney line 293 (Graham et al., J. Gen. Virol. 36 (1977) 59), which contains, in particular, integrated in its genome, the left-hand portion of the genome of an Ad 5 adenovirus (12%), may be mentioned. As an example of a line which can be used for the preparation of defective recombinant retroviruses, the CRIP line (Danos and Mulligan, PNAS 85 (1988) 6460) may be mentioned.

Thereafter, the viruses which have multiplied are recovered and purified according to standard techniques of molecular biology.

The subject of the present invention is also a pharmaceutical composition comprising at least one recombinant virus or one nucleic acid corresponding to the site of interaction of a transcription factor with DNA, such as are defined above. More preferably, the invention relates to a pharmaceutical composition comprising at least one double-stranded nucleic acid comprising all or part of the sequence SEQ ID No. 1 or of an active variant of the latter, or a recombinant virus comprising such a nucleic acid.

The pharmaceutical compositions of the invention may be formulated for the purpose of topical, oral, parenteral, intranasal, intravenous, intramuscular, subcutaneous, intraocular, and the like, administration.

Preferably, the pharmaceutical compositions contain vehicles which are pharmaceutically acceptable for an injectable formulation. They can be, in particular, sterile isotonic saline solutions (containing monosodium or disodium phosphate, sodium, potassium, calcium or magnesium chloride, and the like, or mixtures of such salts), or dry, in particular lyophilized compositions which, on adding sterilized water or physiological saline, as appropriate, enable injectable solutions to be made up.

The doses of nucleic acids (sequence or vector) used for the administration may be adapted in accordance with different parameters, and in particular in accordance with the mode of administration used, the pathology in question, the nucleic acid to be expressed or alternatively the desired length of the treatment. Generally speaking, as regards the recombinant viruses according to the invention, the latter are formulated and administered in the form of doses of between $10^4$ and $10^{14}$ pfu/ml, and preferably $10^6$ to $10^{10}$ pfu/ml. The term pfu ("plaque forming unit") corresponds to the infectious power of a solution of virus, and is determined by infecting a suitable cell culture and measuring, generally after 48 hours, the number of plaques of infected cells. The techniques of determination of the pfu titre of a viral solution are well documented in the literature.

Such pharmaceutical compositions may be used in humans for the treatment and/or prevention of neurodegenerative diseases, and especially for the treatment and/or prevention of the neuronal degeneration associated with ischaemia, hypoxia, hypoglycaemia and epileptic fits, or alternatively with cerebral trauma, or for the treatment and/or prevention of Huntington's chorea or of Alzheimer's disease.

The present invention will be described more completely by means of the examples which follow, which are to be regarded as illustrative and non-limiting.

LEGEND TO THE FIGURES

SEQ ID No. 1: Sequence of the TRE Fragment

FIG. 1: Demonstration of the inhibition by the sequence SEQ ID No. 1 of glutamate-induced cell death by measurement of the binding of ouabain. This inhibitory effect is not observed in the presence of the sequence SEQ ID No. 1 mutated at positions 10 (T→G) and 15 (C→T).

Figure 2:
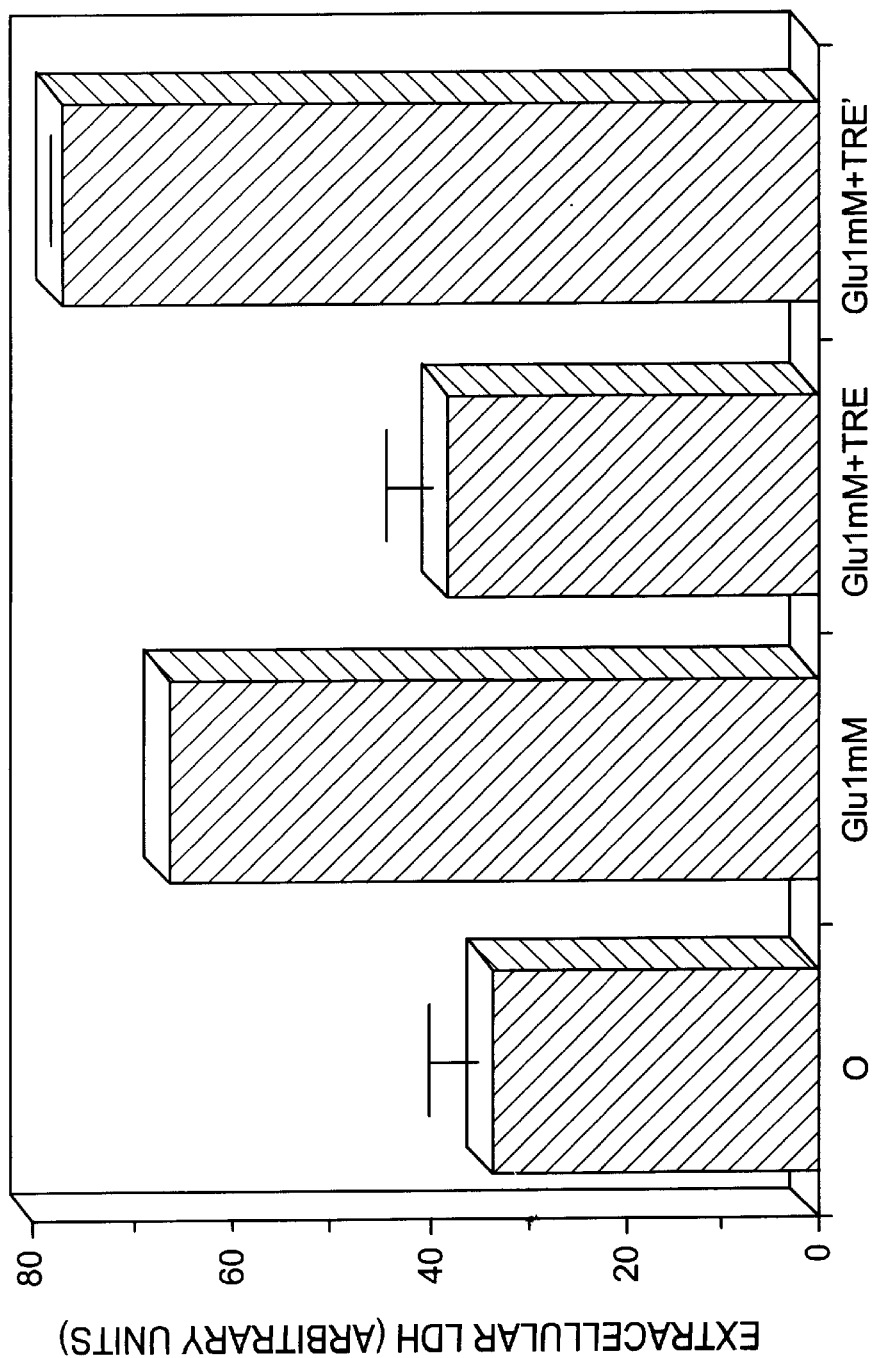

FIG. 2: Demonstration of the inhibition by the sequence SEQ ID No. 1 of glutamate-induced cell death by measurement of the LDH released into the extracellular medium.

This inhibitory effect is not observed in the presence of the sequence SEQ ID No. 1 mutated at positions 10 (T→G) and 15 (C→T).

Figure 3:
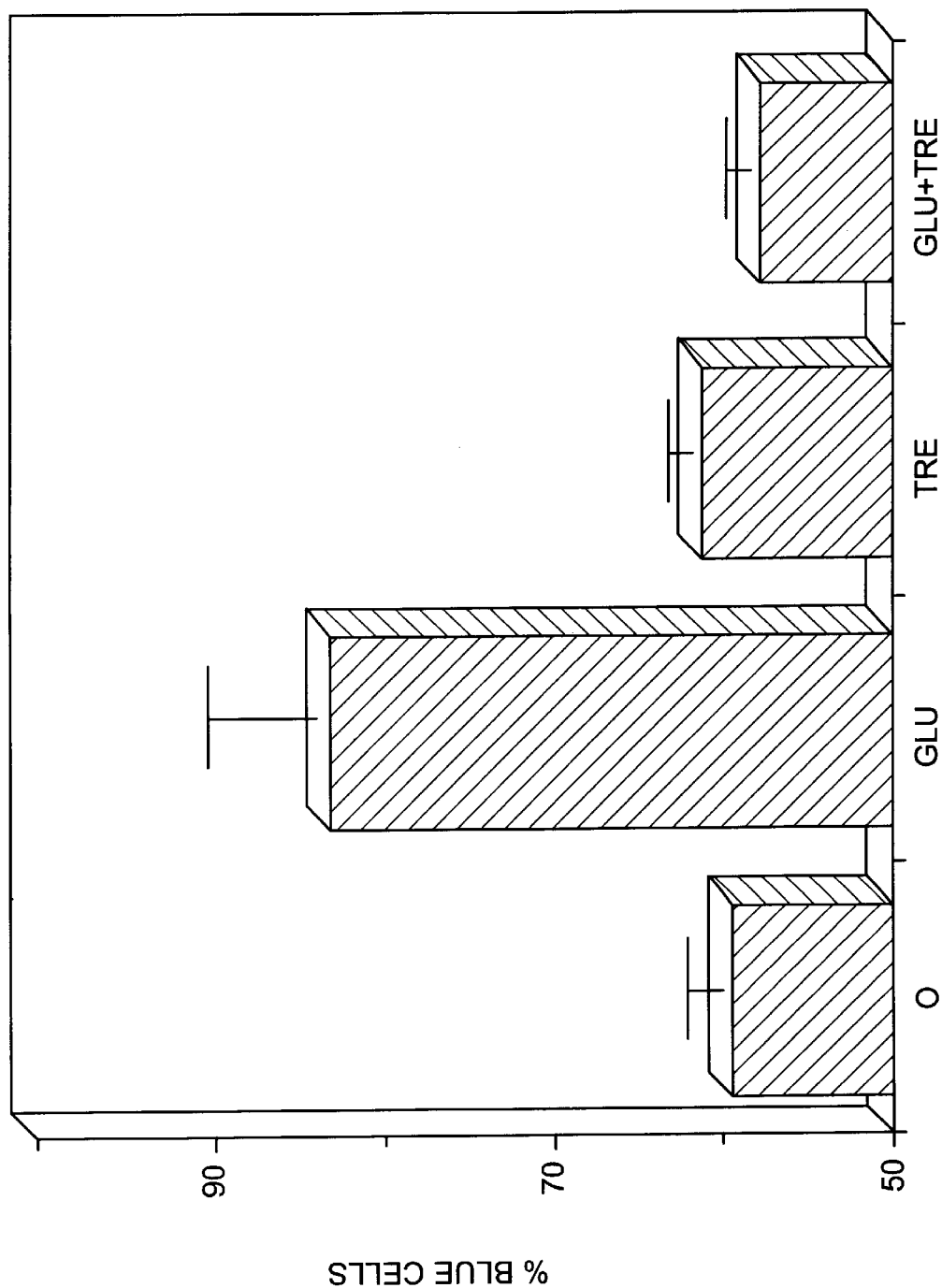

FIG. 3: Demonstration of the inhibition by the sequence SEQ ID No. 1 of glutamate-induced cell death by trypan blue staining.

GENERAL CLONING TECHNIQUES

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol/chloroform extraction of proteins, ethanol or isopropanol precipitation of DNA in a saline medium, transformation in Escherichia coli, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

Filling in of 5' protruding ends may be performed with the Klenow fragment of *E.coli* DNA polymerase I (Biolabs) according to the supplier's specifications. Destruction of 3' protruding ends is performed in the presence of phage T4 DNA polymerase (Biolabs) used according to the manufacturer's recommendations. Destruction of 5' protruding ends is performed by a controlled treatment with S1 nuclease.

In vitro site-directed mutagenesis using synthetic oligodeoxynucleotides may be performed according to the method developed by Taylor et al. [Nucleic Acids Res. 13 (1985) 8749–8764] using the kit distributed by Amersham.

Enzymatic amplification of DNA fragments by the so-called PCR [Polymerase-catalysed Chain Reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

EXAMPLES

Example 1

Demonstration of complexes which bind the sequence SEQ ID No. 1 after exposure of cortical cells to glutamate.

This example demonstrates an increase in the number of intracellular complexes capable of binding the sequence SEQ ID No. 1 after exposure of cortical cells to glutamate. This demonstration was carried out using the gel retardation technique (Lassar et al., Cell 66 (1991) 305).

To this end, cells of embryonic Wistar rat cortex (E17) were isolated according to the method of Dichter (Brain Res. 149 (1978) 279), cultured in Costar 6-well dishes (35 min; density $6 \times 10^5$ cells/dish) in DMEM medium (Dulbecco's Modified Eagle Medium) containing 10 µg/ml insulin, 10 µg/ml transferrin, 10 ng/ml sodium selenite, 10 nM progesterone and 1 nM triiodothyronine, and stored in an incubator (37° C., 5% $CO_2$).

After 4 to 6 days in culture, glutamate is added to the cells. Ten minutes to 48 hours later, the nuclear extracts of the cells were obtained according to the technique described by Lassar et al., cited above. A radioactive probe corresponding to the sequence SEQ ID No. 1 was prepared according to Example 2, and then by labelling with phosphorus-32 according to the technique described by Maniatis (typical specific activity: 50000 cpm/ng). 0.2 ng the the probe thereby obtained are then incubated with 0.5 to 2 µg of nuclear extract, in the presence of 500 ng of poly D(IC)(IC) (Pharmacia) to decrease non-specific binding. The reaction takes place in ice for 10 min. The complexes formed are then visualized by electrophoresis on 5% acrylamide gel. The presence of radioactive bands (demonstrated by autoradiography) demonstrate that glutamate has induced the cellular expression of complexes capable of binding SEQ ID No. 1.

Example 2

Synthesis of the sequence SEQ ID No. 1 and of an inactive variant.

A double-stranded nucleic acid corresponding to the sequence SEQ ID No. 1 was synthesized by means of an automatic nucleotide synthesizer (Maniatis).

An inactive mutant of this nucleic acid was prepared according to the same protocol. This inactive mutant possesses, relative to the sequence SEQ ID No. 1, mutations at positions 10(T→G) and 15(C→T). The absence of activity of this mutant was demonstrated under the same conditions as for Example 1, using this mutant, after radioactive labelling, as probe. The inactivity of this mutant is shown by the absence of a change in its profile of binding to the cell extracts, compared with SEQ ID No. 1, after culturing in the presence of glutamate.

The capacity of the sequence SEQ ID No. 1 to inhibit glutamate-induced death was determined by measurement of three parameters: the binding of tritiated ouabain to neurons in culture, the detection of lactate dehydrogenase in the extracellular medium, and by counting the cells after tryptan blue staining.

Example 3

Measurement of the binding of tritiated ouabain to neurons in culture (FIG. 1).

Ouabain is a ligand for membrane ATPase. It binds only to living neurons. Thus, the higher the amount of ouabain bound, the larger the number of living cells.

Cells of embryonic Wistar rat cortex (E17) were isolated according to the method of Dichter (Brain Res. 149 (1978)

279), cultured in Costar 6-well dishes (35 min; density $6\times10^5$ cells/dish) or 24-well dishes (16 min; density $3\times10^5$ cells/dish) in DMEM medium (Dulbecco's Modified Eagle Medium) containing 10 µg/ml insulin, 10 µg/ml transferrin, 10 ng/ml sodium selenite, 10 nM progesterone and 1 nM triiodothyronine, and stored in an incubator (37° C., 5% $CO_2$). After 4 or 5 days of culture, 2 µM synthetic nucleic acid of sequence SEQ ID No. 1 or of its inactive variant (see Example 2) were added to the culture dishes. After 15 hours of incubation, glutamate (1 mM) was added. The binding of tritiated ouabain to the cultures was evaluated 24 hours after the addition of glutamate, according to the protocol described by Markwell et al., Brain Res. 538 (1991) 1).

The results obtained are presented in FIG. 1. They show clearly that glutamate induces a loss of binding of ouabain to the cells, and that this loss is inhibited in the presence of the synthetic nucleic acid of sequence SEQ ID No. 1, but not in the presence of the inactive mutated variant.

Example 4

Measurement of the release of lactate dehydrogenase into the extracellular medium (FIG. 2).

Lactate dehydrogenase (LDH) is a cytoplasmic enzyme which is released into the extracellular medium by dying cells. Thus, the higher the amount of LDH released, the larger the number of dying cells.

The cells were cultured under the same conditions as in Example 3. The LDH activity present in the extracellular medium was assayed 24 hours after the addition of glutamate according to the method of Berger and Brodia (Sigma procedure 500).

The results obtained are presented in FIG. 2. They show clearly that glutamate induces an increase in the extracellular level of LDH, and that this increase is inhibited in the presence of the synthetic nucleic acid of sequence SEQ ID No. 1, but not in the presence of the inactive mutated variant.

Example 5

Counting of cells after trypan blue staining (FIG. 3).

Trypan blue is a vital stain which enters dead cells, which become "blue", so much say that it is excluded from living cells which remain "white". Thus, the higher the amount of "blue" cells, the larger the number of dead cells.

The cells were cultured under the same conditions as in Example 3. The glutamate concentration used in this example is 5 mM. At the end of incubation, trypan blue was added at a concentration of 0.02%, and the cells were replaced in the incubator for 10 minutes. Every well (6 wells per condition) was then photographed 5 times using a Zeiss 135M microscope. The number of blue and white cells was then counted in blind fashion on each of the photographs.

The results obtained are presented in FIG. 3. They show clearly that glutamate induces considerable cell death, and that this cell death is inhibited in the presence of the synthetic nucleic acid of sequence SEQ ID No. 1.

These results collectively show clearly the capacity of the nucleic acid of the invention to inhibit glutamate-induced neuronal death.

---

---

What is claimed is:

1. A recombinant virus comprising a double-stranded nucleic acid consisting essentially of all or part of sequence SEQ ID No: 1, or a variant thereof, which binds AP1.

2. A recombinant virus according to claim 1, wherein said virus is an adenovirus, a retrovirus, an adeno-associated virus or herpesvirus.

3. A recombinant virus according to claim 2, wherein said adenovirus is a replication defective adenovirus.

4. A recombinant virus according to claim 1, wherein said virus is a replication defective virus.

* * * * *